(12) United States Patent
Zimmerman

(10) Patent No.: US 6,995,237 B1
(45) Date of Patent: Feb. 7, 2006

(54) PREPARATION AND COMPOSITION OF PEPTIDES USEFUL FOR TREATMENT OF AUTOIMMUNE AND TRANSPLANT RELATED GRAFT VERSUS HOST CONDITIONS

(75) Inventor: Daniel H. Zimmerman, Bethesda, MD (US)

(73) Assignee: Cel-Sci Corporation, Vienna, VA (US)

( * ) Notice: Subject to any disclaimer, the term of this patent is extended or adjusted under 35 U.S.C. 154(b) by 325 days.

(21) Appl. No.: 10/111,645

(22) PCT Filed: Oct. 27, 2000

(86) PCT No.: PCT/US00/41646

§ 371 (c)(1), (2), (4) Date: Apr. 26, 2002

(87) PCT Pub. No.: WO01/36448

PCT Pub. Date: May 25, 2001

Related U.S. Application Data

(60) Provisional application No. 60/161,734, filed on Oct. 27, 1999.

(51) Int. Cl.
*A61K 39/00* (2006.01)
*C07K 14/435* (2006.01)

(52) U.S. Cl. .................... 530/324; 514/12; 424/194.1; 424/185.1

(58) Field of Classification Search ................ 530/300, 530/350, 324; 514/12; 424/185.1, 193.1, 424/194.1
See application file for complete search history.

(56) References Cited

U.S. PATENT DOCUMENTS 5,652,342 A * 7/1997 Zimmerman et al. ....... 530/403
5,869,270 A * 2/1999 Rhode et al. .............. 435/7.24

OTHER PUBLICATIONS

Joffre, O et al. Immunobiology [2004] 103(11):4216-4221.*
Weiss, E. in Fundamental Immunology 2nd Edition [1989], ed. by W.E. Paul Raven Press, New York. pp. 359-384.*

* cited by examiner

*Primary Examiner*—Christina Chan
*Assistant Examiner*—F. Pierre VanderVegt
(74) *Attorney, Agent, or Firm*—Sherman & Shalloway

(57) ABSTRACT

Peptide constructs including a first peptide segment which includes an amino acid sequence associated with autoimmune disease, asthma, allergy or xeno- or allograft transplantation rejections bonded directly or via a linker or spacer to a second peptide which binds to T cells and which will redirect the immune response from a harmful Th1 response to a less harmful Th2 response, or which will bind to T cells to initiate, but not complete, an immune response causing the T cells to which the first peptide binds, to undergo anergy and apoptosis, are useful in treating autoimmune conditions. For instance, the peptide construct NGQEEKAGVVST-GLIGGGDSAFDVLSFTAEEKAGVYK (SEQ ID NO:14) wherein Th2 stimulating Peptide G (SEQ ID NO:15) is covalently linked, via spacer GGG, to cardiac myosin molecule My1 (SEQ ID NO:16), can be used for treatment or prevention of myocarditis.

1 Claim, No Drawings

SEQUENCE LISTING

```
<160> NUMBER OF SEQ ID NOS: 52

<210> SEQ ID NO 1
<211> LENGTH: 13
<212> TYPE: PRT
<213> ORGANISM: Artificial Sequence
<220> FEATURE:
<223> OTHER INFORMATION: peptide construct

<400> SEQUENCE: 1

Ile Ala Gly Phe Lys Gly Glu Gln Gly Pro Lys Gly Glu
1               5                   10

<210> SEQ ID NO 2
<211> LENGTH: 8
<212> TYPE: PRT
<213> ORGANISM: Artificial Sequence
<220> FEATURE:
<223> OTHER INFORMATION: peptide construct

<400> SEQUENCE: 2

Lys Asn Ile Val Thr Pro Arg Thr
1               5

<210> SEQ ID NO 3
<211> LENGTH: 15
<212> TYPE: PRT
<213> ORGANISM: Artificial Sequence
<220> FEATURE:
<223> OTHER INFORMATION: peptide construct

<400> SEQUENCE: 3

Gly Asp Lys Val Ser Phe Phe Cys Lys Asn Lys Glu Lys Lys Cys
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: peptide construct
```

```
<400> SEQUENCE: 4

Val Leu Trp Lys Lys Gln Lys Asp Lys Val Ala Glu Leu Glu Asn Ser
1               5                   10                  15
Glu

<210> SEQ ID NO 5
<211> LENGTH: 11
<212> TYPE: PRT
<213> ORGANISM: Artificial Sequence
<220> FEATURE:
<223> OTHER INFORMATION: peptide construct

<400> SEQUENCE: 5

Pro Ser Thr His Val Leu Ile Thr His Thr Ile
1               5                   10

<210> SEQ ID NO 6
<211> LENGTH: 15
<212> TYPE: PRT
<213> ORGANISM: Artificial Sequence
<220> FEATURE:
<223> OTHER INFORMATION: peptide construct

<400> SEQUENCE: 6

Asp Phe Leu Pro His Tyr Lys Asn Thr Ser Leu Gly His Arg Pro
1               5                   10                  15

<210> SEQ ID NO 7
<211> LENGTH: 4
<212> TYPE: PRT
<213> ORGANISM: Artificial Sequence
<220> FEATURE:
<223> OTHER INFORMATION: peptide construct

<400> SEQUENCE: 7

Gly Gly Gly Ser
1

<210> SEQ ID NO 8
<211> LENGTH: 5
<212> TYPE: PRT
<213> ORGANISM: Artificial Sequence
<220> FEATURE:
<223> OTHER INFORMATION: peptide construct

<400> SEQUENCE: 8

Gly Gly Gly Ser Ser
1               5

<210> SEQ ID NO 9
<211> LENGTH: 5
<212> TYPE: PRT
<213> ORGANISM: Artificial Sequence
<220> FEATURE:
<223> OTHER INFORMATION: peptide construct

<400> SEQUENCE: 9

Gly Gly Gly Gly Ser
1               5

<210> SEQ ID NO 10
<211> LENGTH: 6
<212> TYPE: PRT
<213> ORGANISM: Artificial Sequence
<220> FEATURE:
```

-continued

<223> OTHER INFORMATION: peptide construct

<400> SEQUENCE: 10

Gly Gly Gly Gly Ser Ser
1               5

<210> SEQ ID NO 11
<211> LENGTH: 8
<212> TYPE: PRT
<213> ORGANISM: Artificial Sequence
<220> FEATURE:
<223> OTHER INFORMATION: peptide construct

<400> SEQUENCE: 11

Gly Gly Gly Ser Gly Gly Gly Ser
1               5

<210> SEQ ID NO 12
<211> LENGTH: 8
<212> TYPE: PRT
<213> ORGANISM: Artificial Sequence
<220> FEATURE:
<223> OTHER INFORMATION: peptide construct

<400> SEQUENCE: 12

Leu Arg Gly Gly Gly Gly Ser Ser
1               5

<210> SEQ ID NO 13
<211> LENGTH: 9
<212> TYPE: PRT
<213> ORGANISM: Artificial Sequence
<220> FEATURE:
<223> OTHER INFORMATION: peptide construct

<400> SEQUENCE: 13

Val Gln Gly Glu Glu Ser Asn Asp Lys
1               5

<210> SEQ ID NO 14
<211> LENGTH: 37
<212> TYPE: PRT
<213> ORGANISM: Artificial Sequence
<220> FEATURE:
<223> OTHER INFORMATION: peptide construct

<400> SEQUENCE: 14

Asn Gly Gln Glu Glu Lys Ala Gly Val Val Ser Thr Gly Leu Ile Gly
1               5                   10                  15

Gly Gly Asp Ser Ala Phe Asp Val Leu Ser Phe Thr Ala Glu Glu Lys
            20                  25                  30

Ala Gly Val Tyr Lys
        35

<210> SEQ ID NO 15
<211> LENGTH: 15
<212> TYPE: PRT
<213> ORGANISM: Artificial Sequence
<220> FEATURE:
<223> OTHER INFORMATION: peptide construct

<400> SEQUENCE: 15

Asn Gly Gln Glu Glu Lys Ala Gly Val Val Ser Thr Gly Leu Ile
1               5                   10                  15

```
<210> SEQ ID NO 16
<211> LENGTH: 19
<212> TYPE: PRT
<213> ORGANISM: Artificial Sequence
<220> FEATURE:
<223> OTHER INFORMATION: peptide construct

<400> SEQUENCE: 16

Asp Ser Ala Phe Asp Val Leu Ser Phe Thr Ala Glu Glu Lys Ala Gly
1               5                   10                  15

Val Tyr Lys

<210> SEQ ID NO 17
<211> LENGTH: 60
<212> TYPE: PRT
<213> ORGANISM: Artificial Sequence
<220> FEATURE:
<223> OTHER INFORMATION: peptide construct

<400> SEQUENCE: 17

Val Leu Trp Lys Lys Gln Lys Asp Lys Val Ala Glu Leu Glu Asn Ser
1               5                   10                  15

Glu Gly Gly Gly Gly Ser Gln Ala Phe Thr Leu Leu Pro Ser Gly Asp
            20                  25                  30

Ala Leu Pro Ser Leu Leu Arg Gly Gly Gly Ser Ser Gln Val Arg
        35                  40                  45

Leu Gln Pro Arg Gly Met Gly Ala His Ser Pro Gly
        50                  55              60

<210> SEQ ID NO 18
<211> LENGTH: 9
<212> TYPE: PRT
<213> ORGANISM: Artificial Sequence
<220> FEATURE:
<223> OTHER INFORMATION: peptide construct

<400> SEQUENCE: 18

Ala Tyr Met Thr Met Lys Ile Arg Asn
1               5

<210> SEQ ID NO 19
<211> LENGTH: 17
<212> TYPE: PRT
<213> ORGANISM: Artificial Sequence
<220> FEATURE:
<223> OTHER INFORMATION: peptide construct

<400> SEQUENCE: 19

Glu Ile Ile Val Thr His Phe Pro Phe Asp Glu Gln Asn Cys Ser Met
1               5                   10                  15

Lys

<210> SEQ ID NO 20
<211> LENGTH: 31
<212> TYPE: PRT
<213> ORGANISM: Artificial Sequence
<220> FEATURE:
<223> OTHER INFORMATION: peptide construct

<400> SEQUENCE: 20

Ala Tyr Met Thr Met Lys Ile Arg Asn Gly Gly Gly Ser Glu Ile
1               5                   10                  15

Ile Val Thr His Phe Pro Phe Asp Glu Gln Asn Cys Ser Met Lys
            20                  25                  30
```

```
<210> SEQ ID NO 21
<211> LENGTH: 7
<212> TYPE: PRT
<213> ORGANISM: Artificial Sequence
<220> FEATURE:
<223> OTHER INFORMATION: peptide construct

<400> SEQUENCE: 21

Asp Gln Thr Gln Asp Thr Glu
1               5

<210> SEQ ID NO 22
<211> LENGTH: 29
<212> TYPE: PRT
<213> ORGANISM: Artificial Sequence
<220> FEATURE:
<223> OTHER INFORMATION: peptide construct

<400> SEQUENCE: 22

Asp Gln Thr Gln Asp Thr Glu Gly Gly Gly Gly Ser Glu Ile Ile Val
1               5                  10                  15

Thr His Phe Pro Phe Asp Glu Gln Asn Cys Ser Met Lys
            20                  25

<210> SEQ ID NO 23
<211> LENGTH: 27
<212> TYPE: PRT
<213> ORGANISM: Artificial Sequence
<220> FEATURE:
<223> OTHER INFORMATION: peptide construct

<400> SEQUENCE: 23

Pro Ser Thr His Val Leu Ile Thr His Thr Ile Gly Gly Gly Ile Ala
1               5                  10                  15

Gly Phe Lys Gly Glu Gln Gly Pro Lys Gly Glu
            20                  25

<210> SEQ ID NO 24
<211> LENGTH: 15
<212> TYPE: PRT
<213> ORGANISM: Artificial Sequence
<220> FEATURE:
<223> OTHER INFORMATION: peptide construct

<400> SEQUENCE: 24

Asp Phe Leu Pro His Tyr Lys Asn Thr Ser Leu Gly His Arg Pro
1               5                  10                  15

<210> SEQ ID NO 25
<211> LENGTH: 31
<212> TYPE: PRT
<213> ORGANISM: Artificial Sequence
<220> FEATURE:
<223> OTHER INFORMATION: peptide construct

<400> SEQUENCE: 25

Asp Phe Leu Pro His Tyr Lys Asn Thr Ser Leu Gly His Arg Pro Gly
1               5                  10                  15

Gly Gly Ile Ala Gly Phe Lys Gly Glu Gln Gly Pro Lys Gly Glu
            20                  25                  30

<210> SEQ ID NO 26
<211> LENGTH: 33
<212> TYPE: PRT
```

```
<213> ORGANISM: Artificial Sequence
<220> FEATURE:
<223> OTHER INFORMATION: peptide construct

<400> SEQUENCE: 26

Asn Gly Gln Glu Glu Lys Ala Gly Val Val Ser Thr Gly Leu Ile Gly
1               5                   10                  15

Gly Gly Gly Ser Ile Ala Gly Phe Lys Gly Glu Gln Gly Pro Lys Gly
            20                  25                  30

Glu

<210> SEQ ID NO 27
<211> LENGTH: 32
<212> TYPE: PRT
<213> ORGANISM: Artificial Sequence
<220> FEATURE:
<223> OTHER INFORMATION: peptide construct

<400> SEQUENCE: 27

Asp Gly Gln Glu Glu Lys Ala Gly Val Val Ser Thr Gly Leu Ile Gly
1               5                   10                  15

Gly Gly Gly Ser Ile Ala Gly Phe Lys Gly Glu Gln Gly Pro Lys Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: peptide construct

<400> SEQUENCE: 28

Asp Asn Gln Leu Leu Glu Thr Cys Lys Gln Asp Arg Leu Arg Asn Arg
1               5                   10                  15

Arg Gly Asn Gly Ser Ser Thr His Phe Glu Gly Asn Leu Pro Cys
            20                  25                  30

<210> SEQ ID NO 29
<211> LENGTH: 55
<212> TYPE: PRT
<213> ORGANISM: Artificial Sequence
<220> FEATURE:
<223> OTHER INFORMATION: peptide construct

<400> SEQUENCE: 29

Asp Asn Gln Leu Leu Glu Thr Cys Lys Gln Asp Arg Leu Arg Asn Arg
1               5                   10                  15

Arg Gly Asn Gly Ser Ser Thr His Phe Glu Gly Asn Leu Pro Cys Gly
            20                  25                  30

Gly Gly Gly Ser Asp Ser Ala Phe Asp Val Leu Ser Phe Thr Ala Glu
        35                  40                  45

Glu Lys Ala Gly Val Tyr Lys
    50                  55

<210> SEQ ID NO 30
<211> LENGTH: 26
<212> TYPE: PRT
<213> ORGANISM: Artificial Sequence
<220> FEATURE:
<223> OTHER INFORMATION: peptide construct

<400> SEQUENCE: 30

Asp Gln Thr Gln Asp Thr Glu Gly Gly Gly Gly Ser Ser Val His Phe
```

-continued

```
                1               5                  10                 15
Phe Lys Asn Ile Val Thr Pro Arg Thr Pro
                20                 25
```

<210> SEQ ID NO 31
<211> LENGTH: 28
<212> TYPE: PRT
<213> ORGANISM: Artificial Sequence
<220> FEATURE:
<223> OTHER INFORMATION: peptide construct

<400> SEQUENCE: 31

```
Asp Gln Thr Gln Asp Thr Glu Gly Gly Gly Ser Ser Gly Asp Lys
1               5                  10                 15
Val Ser Phe Phe Cys Lys Asn Lys Glu Lys Lys Cys
                20                 25
```

<210> SEQ ID NO 32
<211> LENGTH: 30
<212> TYPE: PRT
<213> ORGANISM: Artificial Sequence
<220> FEATURE:
<223> OTHER INFORMATION: peptide construct

<400> SEQUENCE: 32

```
Asp Gln Thr Gln Asp Thr Glu Gly Gly Gly Ser Ser Tyr Gln Gln
1               5                  10                 15
Leu Asn Ser Glu Arg Gly Val Pro Asn Glu Asn Ile Glu Asn
                20                 25                 30
```

<210> SEQ ID NO 33
<211> LENGTH: 42
<212> TYPE: PRT
<213> ORGANISM: Artificial Sequence
<220> FEATURE:
<223> OTHER INFORMATION: peptide construct

<400> SEQUENCE: 33

```
Val Leu Trp Lys Lys Gln Lys Asp Lys Val Ala Glu Leu Glu Asn Ser
1               5                  10                 15
Glu Gly Gly Gly Gly Ser Ser Ile Gln Thr Gln Met Lys Thr Tyr Ser
                20                 25                 30
Asp Ile Asp Gly Lys Leu Val Ser Glu Val
        35                 40
```

<210> SEQ ID NO 34
<211> LENGTH: 36
<212> TYPE: PRT
<213> ORGANISM: Artificial Sequence
<220> FEATURE:
<223> OTHER INFORMATION: peptide construct

<400> SEQUENCE: 34

```
Val Leu Trp Lys Lys Gln Lys Asp Lys Val Ala Glu Leu Glu Asn Ser
1               5                  10                 15
Glu Gly Gly Gly Gly Ser Ser Val Phe Ile Lys Arg Val Ser Asn Val
                20                 25                 30
Ile Ile His Gly
        35
```

<210> SEQ ID NO 35
<211> LENGTH: 38
<212> TYPE: PRT

```
<213> ORGANISM: Artificial Sequence
<220> FEATURE:
<223> OTHER INFORMATION: peptide construct

<400> SEQUENCE: 35

Val Leu Trp Lys Lys Gln Lys Asp Lys Val Ala Glu Leu Glu Asn Ser
1               5                   10                  15

Glu Gly Gly Gly Gly Ser Ser Met Lys Val Thr Val Ala Phe Asn Gln
            20                  25                  30

Phe Gly Pro Asn Arg Arg
            35

<210> SEQ ID NO 36
<211> LENGTH: 38
<212> TYPE: PRT
<213> ORGANISM: Artificial Sequence
<220> FEATURE:
<223> OTHER INFORMATION: peptide construct

<400> SEQUENCE: 36

Val Leu Trp Lys Lys Gln Lys Asp Lys Val Ala Glu Leu Glu Asn Ser
1               5                   10                  15

Glu Gly Gly Gly Gly Ser Ser Ile Ala Ser Arg Arg Val Asp Gly Ile
            20                  25                  30

Ile Ala Ala Tyr Gln Asn
            35

<210> SEQ ID NO 37
<211> LENGTH: 42
<212> TYPE: PRT
<213> ORGANISM: Artificial Sequence
<220> FEATURE:
<223> OTHER INFORMATION: peptide construct

<400> SEQUENCE: 37

Val Leu Trp Lys Lys Gln Lys Asp Lys Val Ala Glu Leu Glu Asn Ser
1               5                   10                  15

Glu Gly Gly Gly Gly Ser Ser Ile Asp Ile Phe Ala Ser Lys Asn Phe
            20                  25                  30

His Leu Gln Lys Asn Thr Ile Gly Thr Gly
            35                  40

<210> SEQ ID NO 38
<211> LENGTH: 35
<212> TYPE: PRT
<213> ORGANISM: Artificial Sequence
<220> FEATURE:
<223> OTHER INFORMATION: peptide construct

<400> SEQUENCE: 38

Val Leu Trp Lys Lys Gln Lys Asp Lys Val Ala Glu Leu Glu Asn Ser
1               5                   10                  15

Glu Gly Gly Gly Gly Ser Ser Tyr Phe Val Gly Lys Met Tyr Phe Asn
            20                  25                  30

Leu Ile Asp
        35

<210> SEQ ID NO 39
<211> LENGTH: 38
<212> TYPE: PRT
<213> ORGANISM: Artificial Sequence
<220> FEATURE:
<223> OTHER INFORMATION: peptide construct
```

-continued

```
<400> SEQUENCE: 39

Asp Gln Thr Gln Asp Thr Glu Gly Gly Gly Ser Ser Gly Ile Gly
1               5                   10                  15

Ala Val Leu Lys Val Leu Thr Thr Gly Pro Ala Leu Ile Ser Trp Ile
            20                  25                  30

Lys Arg Lys Arg Gln Gln
            35

<210> SEQ ID NO 40
<211> LENGTH: 13
<212> TYPE: PRT
<213> ORGANISM: Artificial Sequence
<220> FEATURE:
<223> OTHER INFORMATION: peptide construct

<400> SEQUENCE: 40

Ile Ala Gly Phe Lys Gly Glu Gln Gly Pro Lys Gly Glu
1               5                   10

<210> SEQ ID NO 41
<211> LENGTH: 13
<212> TYPE: PRT
<213> ORGANISM: Artificial Sequence
<220> FEATURE:
<223> OTHER INFORMATION: peptide construct

<400> SEQUENCE: 41

Val His Phe Phe Lys Asn Ile Val Thr Pro Arg Thr Pro
1               5                   10

<210> SEQ ID NO 42
<211> LENGTH: 17
<212> TYPE: PRT
<213> ORGANISM: Artificial Sequence
<220> FEATURE:
<223> OTHER INFORMATION: peptide construct

<400> SEQUENCE: 42

Tyr Gln Gln Leu Asn Ser Glu Arg Gly Val Pro Asn Glu Asn Ile Glu
1               5                   10                  15

Asn

<210> SEQ ID NO 43
<211> LENGTH: 19
<212> TYPE: PRT
<213> ORGANISM: Artificial Sequence
<220> FEATURE:
<223> OTHER INFORMATION: peptide construct

<400> SEQUENCE: 43

Ile Gln Thr Gln Met Lys Thr Tyr Ser Asp Ile Asp Gly Lys Leu Val
1               5                   10                  15

Ser Glu Val

<210> SEQ ID NO 44
<211> LENGTH: 13
<212> TYPE: PRT
<213> ORGANISM: Artificial Sequence
<220> FEATURE:
<223> OTHER INFORMATION: peptide construct

<400> SEQUENCE: 44

Val Phe Ile Lys Arg Val Ser Asn Val Ile Ile His Gly
```

```
                1               5                   10
```

<210> SEQ ID NO 45
<211> LENGTH: 15
<212> TYPE: PRT
<213> ORGANISM: Artificial Sequence
<220> FEATURE:
<223> OTHER INFORMATION: peptide construct

<400> SEQUENCE: 45

```
Met Lys Val Thr Val Ala Phe Asn Gln Phe Gly Pro Asn Arg Arg
1               5                   10                  15
```

<210> SEQ ID NO 46
<211> LENGTH: 15
<212> TYPE: PRT
<213> ORGANISM: Artificial Sequence
<220> FEATURE:
<223> OTHER INFORMATION: peptide construct

<400> SEQUENCE: 46

```
Ile Ala Ser Arg Arg Val Asp Gly Ile Ile Ala Ala Tyr Gln Asn
1               5                   10                  15
```

<210> SEQ ID NO 47
<211> LENGTH: 19
<212> TYPE: PRT
<213> ORGANISM: Artificial Sequence
<220> FEATURE:
<223> OTHER INFORMATION: peptide construct

<400> SEQUENCE: 47

```
Ile Asp Ile Phe Ala Ser Lys Asn Phe His Leu Gln Lys Asn Thr Ile
1               5                   10                  15

Gly Thr Gly
```

<210> SEQ ID NO 48
<211> LENGTH: 12
<212> TYPE: PRT
<213> ORGANISM: Artificial Sequence
<220> FEATURE:
<223> OTHER INFORMATION: peptide construct

<400> SEQUENCE: 48

```
Tyr Phe Val Gly Lys Met Tyr Phe Asn Leu Ile Asp
1               5                   10
```

<210> SEQ ID NO 49
<211> LENGTH: 25
<212> TYPE: PRT
<213> ORGANISM: Artificial Sequence
<220> FEATURE:
<223> OTHER INFORMATION: peptide construct

<400> SEQUENCE: 49

```
Gly Ile Gly Ala Val Leu Lys Val Leu Thr Thr Gly Pro Ala Leu Ile
1               5                   10                  15

Ser Trp Ile Lys Arg Lys Arg Gln Gln
            20                  25
```

<210> SEQ ID NO 50
<211> LENGTH: 15
<212> TYPE: PRT
<213> ORGANISM: Artificial Sequence
<220> FEATURE:
<223> OTHER INFORMATION: peptide construct

```
<400> SEQUENCE: 50

Asp Gly Gln Glu Glu Lys Ala Gly Val Val Ser Thr Gly Leu Ile
1               5                   10                  15

<210> SEQ ID NO 51
<211> LENGTH: 13
<212> TYPE: PRT
<213> ORGANISM: Artificial Sequence
<220> FEATURE:
<223> OTHER INFORMATION: peptide construct

<400> SEQUENCE: 51

Asp Leu Leu Lys Asn Gly Glu Arg Ile Glu Lys Val Glu
1               5                   10

<210> SEQ ID NO 52
<211> LENGTH: 12
<212> TYPE: PRT
<213> ORGANISM: Artificial Sequence
<220> FEATURE:
<223> OTHER INFORMATION: peptide construct

<400> SEQUENCE: 52

Gly Gly Gly Ser Gly Thr Gly Ser Gly Ser Gly Ser
1               5                   10
```

PREPARATION AND COMPOSITION OF PEPTIDES USEFUL FOR TREATMENT OF AUTOIMMUNE AND TRANSPLANT RELATED GRAFT VERSUS HOST CONDITIONS

The appln claims the benefit of 60/161,734 filed on Oct. 27, 1999.

FIELD OF INVENTION

This invention relates to peptide constructs, i.e., polypeptides obtained by linking together two or more peptides based on or derived from different molecules, which are useful in the treatment or prevention of autoimmune diseases, asthma, allergies, and host versus graft (or graft versus host) rejection, as well as to compositions containing same, methods for producing same and methods for using same.

BACKGROUND

Autoimmune conditions are characterized by the body attacking itself by mounting an immune response against itself. Various antigens often with defined epitopes recognized for some HLA genotypes, have been identified, including those associated with insulin dependent diabetes mellitus (IDDM), rheumatoid arthritis (RA) [e.g., collagen type II 390–402 IAGFKGEQGPKGE (SEQ ID NO:1), systemic lupus erythematousis (SLE), ankyosing spondylitis (AS), pemphius vulgaris (PV) [epidermal cell adhesion molecule desmoglein 190–204], multiple sclerosis (MS), Myelinproteolipid MPL [peptide sequence KNIVTPRT (SEQ ID NO:2], certain types of psoriasis, and uveoretintis (J. Hammer et al 1997, Adv. Immunol, 66:67; R. Tisch, et al, 1999, J. Immunol. 163:1178; J. Yoon, et al, 1999, Science 284: 1183; P. J. Ruiz et al, 1999, J. Immunol., 162:3336; C. J. Krco, et al, 1999, J. Immunol. 163:1661). In other cases, peptides are known that induce in animals, a condition similar to ones found in humans, such as GDKVSFFCKNKEKKC (SEQ ID NO:3) for antiphospholipid antibodies associated with thrombosis (A. Gharavi et al, 1999, J. Immunol., 163:2922) or Myelin peptides for experimental autoimmune encephalitis as a model for MS (P. J. Ruiz, et al, 1999, J. Immunol., 162:3336; S. Araga, et al, 1999, J. Immunol., 163:476–482; N. Karin, et al, 1999, J. Immunol., 160:5188; L. M. Howard, et al, 1999, J. Clin. Invest., 103:281). Glutamic acid decarboxylase and specific peptides have been identified for IDDM (R. Tisch, et al, 1999, J. Immunol., 163:1178; J. Yoon, et al, 1999, Science, 284: 1183). Many of these conditions are also characterized by elevated levels of one or more different cytokines and other effectors such as TNF (S. Kleinau, et al, 1999, J. Immunol. 162:4266; T. Preckel, et al, 1998, Eur. J. Immunol., 28:3706; P. Wooley, et al, 1992, J. Immunol., 151:6602) as well as autoantibodies, including in some cases, anti-costimulator molecules, in particular, those for CTLA-4 (CD152) on CD4+ cells (T. Matsui, et al, 1999, J. Immunol., 162:4328).

Efforts are underway to attack cells or cellular products of the immune system and thereby treat autoimmune conditions, allergies, asthma and tranplantation rejection using as reagents presumptive antigenic peptides or proteins, peptides representing certain T cells, monoclonal antibodies, recombinant proteins binding various effector cells or molecules such as TNF and IgE.

The following immunomodulatory approach contrasts with the mode of action for products which are antigen specific.

A fusion protein LFA-3TIP (Amevive™ from Biogen), purportedly a molecule composed of the first extracellular domain of LFA-3 fused to the hinge (CH2 and CH3 domains of human IgG1) which targets the CD2 receptor on T cells, is being evaluated for psoriasis and for xeno- and allograft rejection. LFA-3TIP is bifunctional (i.e., two identical LFA-3 regionsand TIP) and, therefore is a complex conjugate molecule. According to Biogen, LFA-3TIP is a recombinant fusion protein designed to modulate immune response by blocking the cellular pathway that activates T cells. It is presumed by the present inventor that the compound is acting on a subset of memory effector cells with a down modulation or re-direction of modulation activity.

These less antigen specific approaches also utilize monoclonal antibodies that act on activated T cells and down regulate them such as by anti-CD3 (Protein Design Laboratories) or block APC and T cell interaction by anti-ICAM-3 (ICOS). MEDI-507 (Medimmune) is believed to be a humanized monoclonal antibody, for psoriasis that also targets CD2, presumably for removing or inactivating those cell types. Other diseases, such as, tissue transplantation rejection and allergies are also being tested by this approach. In contrast to acting on cell surface markers, rhu-Mab-E25 (Genentech) is believed to be a humanized monoclonal antibody against IgE that binds to circulating IgE, with the goal of preventing activation of mast cells. In contrast, other researchers are developing monoclonal antibodies to act on symptoms or agents directly causing disease symptoms. Remicade Infliximab (Centocor) is purported to be a monoclonal antibody to TNF. Anti CD40 ligand has been used for treatment in animal model of MS (L. M. Howard, et al., 1999, J. Clin. Invest, 103:281). A recombinant generated designed protein Enbrel (Immunex) is purported to comprise two molecules of r-DNA derived TNF receptor, and is intended to block TNF's action.

It should be noted, however, that many of these agents are not sufficiently disease specific and often recognize and could affect normal cellular and body constituents that have a defined and necessary role in normal immune defenses which are still needed.

More antigen or disease specific approaches are exemplified by the attempt to treat MS patients by oral administration of myelin proteins which have recently been reported; the same group of searchers are also using collagen type II for treatment of patients with rheumatoid arthritis. These treatments are designed to attack at the level of the gut associated lymphoid tissues (GALT) to induce tolerance by antigen specific suppression of the immune system. It is not known if these treatments use the intact protein or a hydrolyzate containing smaller peptides. See D. Hafler, et al, 1988, J. Immunol., 141:181; K. Wucherpfennig, et al, 1990, Science, 248:1016; K. Ota, et al., 1990, Nature, 346;183; and H. Weiner, 1999, PNAS, 88:9161.

Several researchers are testing peptide based materials for treatment of autoimmune conditions. One approach uses peptide as immunogen, given orally in large quantities. The peptide represents a peptide sequence that is thought to be the autoimmune epitope itself or a modified form which may also have altered binding or improved stability properties. By use of the peptide it is thought that either the normal peptide or an altered peptide ligand (APL) will bind to the T cell receptor (TCR) and induce a state of anergy since the multiple sets of bindings that would occur with antigen presentation with an antigen presenting cell (APC) do not occur (A. Faith, et al., 1999, J. Immunol., 162:1836; Soares, et al, 1998, J. Immunol., 160:4768; M. Croft, et al, 1997, J. Immunol., 159:3257: L. Ding, et al., 1998, J. Immunol., 161:6614; and S. Hin, et al, 1999, J. Immunol., 163:2363). Some of the approaches with APL include using related amino acids such a D amino acids (U. Koch, et al, 1998, J. Immunol., 161:421), amino acids with substituted side chains (R. De Palma, et al, 1999, J. Immunol., 162:1982), methylene groups to replace peptide bonds in the peptide backbone (L. Meda, et al, 1996, J. Immunol., 157:1213) and N-hydroxyl peptides (S. Hin et al, J. Immunol., 163:2363). Several groups have studied the effect of various substitutions of side chains and the MHC and TCR molecules (L. Raddrizani, et al, 1997, J. Immunol., 159:702; T. M. Clay, et al, 1999, J. Immunol., 162:1749; L. Radrizanni, et al., Eur. J. Immunol., 1999, 29:660). With insulin activity it has been shown that a one amino acid change on the β- chain can abolish its oral immune tolerance activity in two (2) mechanistically different IDDM murine models (D. Homann, et al, 1999, J. Immunol., 163:1833). While not an autoimmune epitope it has been reported that a single change from threonine to alanine can abolish biological activity (C. L. Sutherland, et al, 1999, J. Immunol., 162:4720); a switch from phenylalanine to alanine alters the bee venom phospholipase to an inactive form (A. Faith, et al, 1999, J. Immunol, 162:1836); as does a switch from tyrosine to alanine change from active to inactive for another system (S. Hausman, et al, 1999, J. Immunol., 162:5389).

In another approach based on peptide materials, truncated peptides of autoimmune inducing epitope are used as antagonist in an animal model to treat the particular condition (N. Karin, et al, 1999, J. Immunol., 160:5188). Several groups are using synthetic amino acid polymers that are considered to represent epitopes which contain Tyrosine (Y), Glutamic acid (E), alanine (A) and lysine (K) to target T cells such as Copolymer 1. In one study Copaxone is being used as an oral tolerance delivery approach to treat MS patients. Copaxone is believed to be a synthetic copolymer of four amino acids (D. Hafler, et al, 1988, J. Immunol., 141:131). Modified peptides of peptide epitopes are reportedly being studies for treatment of various autoimmune conditions, including MS and PV (desmoglein-3) (J. Hammer, et al, 1997, Adv. Immunol., 66:67; K. Wucherpfennig, et al, 1995, PNAS, 92:11935). The scientists doing these studies may also be using Myelin proteolipid associated peptide epitope, a polymer or derivative of this epitope for MS, (Wucherpfennig, et al, Id.).

Peptides that are unique to the T cell antigen receptor molecule are found in a particular part of the variable region, usually the third hypervariable region of the beta chain of the T cell antigen Receptor (TCRβVX) (B. Kotzin, et al, 1991, PNAS, 88:9161; J. Oksenberg, et al, 1990, Nature, 345:344; S. Zamil, et al, 1986, Nature, 324:258). One such peptide is apparently being evaluated for a psoriasis vaccine as IR 502 and others for rheumatoid arthritis (D. P. Gold, et al, 1997, J. Neuroimmunology, 76:29). In this case an immune response to the TCRβV3 (C. L. Sutherland, et al, 1999, J. Immunol., 162:4720) peptide is generated with the goal to have the body eliminate the particular T cells and by so removing the T cells responsible for the condition, treating the condition. However, this approach has the potential of eliminating other T cells that contain the same βV3 peptide sequence besides the one responsible for the autoimmune condition.

Still another peptide approach uses complimentary peptide vaccine that induces T cell anergy and prevents Experimental Autoimmune Encephalitis (EAE) in rats by induction of anti-TCR antibodies (a la anti-idiotype) and thereby elimination of these cells (S. Araga, et al, 1999, J. Immunol., 163:476).

The present inventor has previously discovered and described immunomodulatory peptide constructs which include a first peptide which is an antigenic peptide associated with disease or the causative organism of disease covalently bonded to a second peptide which is a T cell binding ligand. These heterofunctional cellular immunological reagents are described in the commonly assigned U.S. Pat. No. 5,652,342, the disclosure of which is incorporated herein, in its entirety, by reference thereto. According to this patent, representative T cell binding ligands include, for example, portions of MHC Classes I and II, such as, b-2-microglobulin, portions of LFA-3, portions of the Fc region of the heavy chain of immunoglobulins, Ia$^+$ molecules, Among the general disclosure of antigens associated with disease, mention is made of antigens associated with auto-immunity, including diabetes, Rheumatoid arthritis and thyroiditis.

SUMMARY OF THE INVENTION

The present invention provides peptide constructs useful for treatment of autoimmune disease, asthma, allergy, and tissue transplantation rejection (including both host-versus-graft and graft-versus-host rejection), which differ from the above approaches used with antigenic peptide alone. The novel constructs bind in an antigen specific manner and redirect the T cell in the direction of a nondeleterious autoimmune response, primarily from a Th1 to a Th2 immune response, but where advantageous, primarily from a Th2 to a Th1 immune response. Alternatively, the novel constructs include one peptide component which will bind to T cells associated with autoimmune disease, asthma, allergies or host versus graft or graft versus host rejection while a second peptide component will bind to sites on the T cells which will preclude the normal sequence of events required for cell activation thereby initiating an abortive T cell modulation resulting in cell anergy and apoptosis.

Specifically, the novel peptides of this invention include peptide constructs of the following formula (I):

$$P_1\text{-}x\text{-}P_2 \qquad (I)$$

where $P_1$ is a peptide associated with autoimmune disease, allergy or asthma, or tissue transplantation rejection and which will bind to an antigen receptor on a set or subset of T cells;

$P_2$ is an immune response modifying peptide which will
(i) cause a directed immune response by said set or subset of T cells to which the peptide $P_1$ is attached or
(ii) bind to a T cell receptor which will cause said set or subset of T cells to which the peptide $P_1$ is attached to initiate, but not complete, an immune response causing said set or subset of T cells to undergo anergy and apoptosis; and x is a direct bond or linker for covalently bonding $P_1$ and $P_2$.

The present invention also provides a first method for treating or preventing inappropriate autoimmune response in individuals at risk for autoimmune disease, allergic reactions, asthma or host-graft or graft-host rejection, wherein a pharmacologically effective amount of a peptide construct of formula (I) is administered to the individual to effectively eliminate the set or subset of T cells involved in the autoimmune response.

The present invention also provides a second method for modulating an inappropriate autoimmune response in individuals at risk for autoimmune disease, allergic reactions, asthma or host-graft or graft-host rejection, wherein a pharmacologically effective amount of a peptide construct of formula (I) is administered to the individual to redirect the autoimmune response from a Th1 to a Th2 immune response, or from a Th2 to a Th1 immune response, whereby the inappropriate autoimmune response is modulated to decrease or eliminate the adverse effects associated with the inappropriate autoimmune response.

DETAILED DESCRIPTION OF THE INVENTION

It has been reported that the, "failure of mature CD8 cells to simultaneously engage their TCR and CD8 coreceptor triggers an activation process that begins with inhibition of CD8 gene expression through remethylation and concludes with up-regulation of surface fas and fas ligand and cellular apoptosis" (G. A. Pestano, et al, 1999, Science, 284:1187). This is consistent with the results of others where if full engagement of certain very major coreceptors are not effected then an activation process, but abortative in nature, leading to apoptosis occurs (see also P. Gogolak, et al, 1996, Immunol. Let. 54:135; Grakoui, et al, 1999, Science, 284: 221; Malissen, 1999, Science, 285:207; S. Redpath, et al, 1999, J. Immunol., 163:6; T. Preckel, et al, 1998, Eur. J. Immunol., 28:3706; S. Sambhara, et al, 1991, Science, 252:1424; H. Kishimoto, et al, 1999, J. Immunol., 163:1817; Kubo, et al, 1999, J. Immunol., 163:2432). Therefore, a different approach would be to have a modulation but not with a full sequence of events, the construct binding in an antigen specific manner with the antigenic epitope but the TCBL ligand binding to a site on another molecule associated with certain early events that are early intermediates in the full expression pathway thereby occupying the space and causing an early event in the process of activation (such as $Ca^{++}$ flux, activation of various phosphatases, membrane migration events, such as "patching" or "capping", changes in RNA metabolism) but not supporting the complete activation process which can be thought of as culminating by antigen specific non-antibody mediated Cytotoxic T Lymphocyte activity such as killing of infected or tumor cells, DNA synthesis and cell division, and cytokine secretion, namely, without allowing the ultimate tertiary complex of binding events (MHC, antigen TCR and CD4 (or CD8)) necessary for full activation by being out of the normal temporal sequence of events. Perhaps this early binding would be of such strength that it does not disassociate and allow the cell surface rearrangement necessary for the full and normal sequence of modulatory events, such as, proliferation or secretion of late cytokines such as Fas, TNF-α or IFN-γ and thereby prohibiting events found in an autoimmune disease associated pathway with complete T cell activation. For example, initially after antigen binding to the TCR ICAM-1 (also known as CD54) on APC binding to a T cell's LFA-1 (also known as CD11a/CD18) and then is shifted away and a rearrangement with clustering of the MHC and antigenic peptides on APC binding eventually by migration on T cell membrane to a clustering of TC and CD4 (or CD8) (B. Malissen, 1999, Science, 285:207; A. Grakoui, et al, 1999, Science, 285:221).

According to one embodiment of this invention, such rearrangement is prevented by the close association in a peptide construct using a TCBL from ICAM-1, LFA-3 (aa26–42), VLWKKQKDKVAELENSE (SEQ ID NO:4) (L. Osborn, et al, 1995, JEM, 181:429), by either the disparity in the temporal binding or higher strength of binding activity, thereby preventing the rearrangements and other more intimate interactions necessary for activation. Initially these sites are close together but normally rearrangements on the T cell surface occur during the activation process so by preventing this shift activation should not occur. Likewise, a TCBL from CD4 that binds to the TCR and CD3 may be used as the TCBL in the peptide construct of this invention. Its binding to the T cell recognition site will inhibit subsequent events from occurring (MHC II with CD4 or β-2 with CD8).

Still another approach is a construct which redirects the immune response initiated by the natural autoimmune inducing event from a TH1 to a TH2 response (see, e.g., Lowrie, et al, 1999, Nature, 400:269; R. Tisch, et al, 1999, J. Immunol., 163:1178). As used herein, a TH2 directed response is one which directs the immune-response toward the TH2 direction, thus favoring production of more IL-5, IL-4, TNF-α-cytokines and antibody isotypes IgG1 and IgG3 in mice (or comparables in man) as opposed to Th1, where the immune response favors production of IFN-γ, IL-2, IL-6, IL-12 cytokines and antibody isotypes IgG2a and IgG2b in mice and Cytotoxic T cell activity. It is understood, of course, that a "TH2 directed response" is not intended to imply an exclusively TH2 response, but rather a mixed immune response which is weighted to favor a TH2 profile.

According to this embodiment a TCBL associated with TH2 responses; e.g., peptide G from MHC class II (D. Zimmerman, et al, 1996, Vacc. Res., 5:91, 5:102; K. Rosenthal, et al, 1999, Vaccine), IL-4 or IL-5 or peptides known to stimulate I1–4 or IL-5 synthesis are used as the TCBL along with the autoimmune inducing peptide (see, e.g., Hammer, et al, Krco, et al, Araga, et al, Ota, et al, Ruiz, et al, Yoon, et al, supra, Dittel, et al, 1999, J. Immunol., 163:32; Gautam, et al, 1998, J. Immunol., 161:60, the disclosures of which are incorporated herein by reference thereto) in the peptide conjugate. These peptide constructs may be used, for example, to treat type I diabetes. In an animal model the mechanism of diabetes prevention in the RIP-NP model was shown to be mediated by insulin β-chain, and I1–4 producing regulatory cells acting as bystander suppressors (D. Homann, et al, 1999, J. Immunol., 163: 1833). Such redirection of immune responses have been previously reported by a DNA vaccine for TB which redirected the immune response from an inefficient response TH2 to a response that was a very effective Th1 (Lowrie, et al, 1999, Nature, 400:269). Thus, redirecting an already existing immune response from a TH1 to a TH2 would be effective for treating autoimmune related diseases. A TCBL involved in CD28 costimulation (Kubo, et al, supra) could also be effective for this purpose. If, on the otherhand, the need was to redirect from a TH2 to a TH1, much less likely to be needed since many autoimmune conditions are thought to be the manifestation of deleterious TH1 effects, then a TCBL such as peptide J DLLKNGERIEKVE (SEQ ID NO:51) (D. Zimmerman, et al, supra; K. Rosenthal, et al, supra) or ones known to stimulate IL-2 or IL-12 synthesis, would be used along with the autoimmune inducing peptide.

Yet another approach is to use the peptide construct to not activate the normal immune process but to activate the process leading to apoptosis of the T cell by using as the TCBL a ligand that binds to a site on the T cell whose normal binding and activation leads to apoptosis of the T cell; such as the TNF- receptor of the T cell, in which the TCBL would be the TNF-α ligand portion. Examples of such TNF peptides known to activate macrophages are amino acids 70–80 PSTHVLITHTI (SEQ ID NO:5) (W. J. Britton, et al, 1998, I & I, 66:2122) and perhaps the antagonist peptide represented by DFLPHYKNTSLGHRP (SEQ ID NO:6) of another region (C. Chirinos-Rojas, et al, 1998, J. Immunol., 161:5621). It has been suggested in WO 99/36903A1 that the H4-1-BB Ligand is useful as a treatment for autoimmune disease similar to uses for flt3-L and CD40L; therefore, H4-1BB may also be used as TCBL for inclusion with autoimmune antigens to form the inventive peptide construct. Other such TCBL examples are available from application with Fas and Fas-ligand including the noncleavable Fas-ligand (WO 99/36079A1).

Since autoimmune reactive cells in disease are most likely already activated and may be expressing Fas (Y. Tomita, et al, 1996, int. J. Can., 68:132; B. Lie, et al, 1996, Biol. Pharma. Bul. 19:1602) the Fas-Ligand or the sequence obtained by reverse engineering technique to determine amino acid (aa) sequence acting as receptor for DEVD-aldehyde or YVAD chloromethylketone, may also be used as the TCBL. Representatives from another pair, IFN-γ and the IFN-γ ligand can also be used as TCBLs in the invention peptide constructs.

In this invention the antigenic peptide and the peptide for T cell binding (TCBL) may be directly linked together in any order (i.e., N-terminal of one to C-terminal of other or vice versa) or the peptide may be covalently bonded by a spacer or linker molecule. With regard to linkers between the two domains, suitable examples include a thioether bond between an amino terminus bromoacetylated peptide and a carboxyl terminus cysteine, often preceded by a diglycine sequence (D. Zimmerman, et al, supra), carbodiimide linkages, a multiple glycine, e.g., from 3 to 6 glycines, such as triglycine, with or without one or two serines, separation between the two entities, e.g., GGGS (SEQ ID NO:7), GGGSS (SEQ ID NO.8), GGGGS (SEQ ID NO:9), GGGGSS (SEQ ID NO.10), GGGSGGGS (SEQ ID NO:11), etc., and other conventional linkages, such as, for example, the direct linkages such as, EDS, SPDP, and MBS, as disclosed in the aforementioned U.S. Pat. No. 5,652,342.

Thus, the peptide constructs of this invention may be conveniently represented by the following formula (I):

$$P_1\text{-}x\text{-}P_2 \qquad (1)$$

where $P_1$ is a peptide associated with autoimmune disease, allergy or asthma, or transplantation rejection and which will bind to an antigen receptor on a set or subset of T cells;

$P_2$ is an immune response modifying peptide which will bind to T cells to cause a directed immune response by said set or subset of T cells to which the peptide $P_1$ is attached or which will bind to a T cell receptor which will cause said set or subset of T cells to which the peptide $P_1$ is attached to initiate, but not complete, an immune response causing said set or subset of T cells to undergo anergy and apoptosis; and x is a direct bond or linker for covalently bonding $P_1$ and $P_2$.

The TCBL portion of the immunomodulatory peptide construct of this invention, i.e., $P_2$, may comprise a discontinuous epitope composed of two small regions separated by a loop or by a single chain short peptide in place of the loop (D. Shan, et al, 1999, J. Immunol., 162:6589). For example, an eight amino acid group, LRGGGGSS (SEQ ID NO:12), of 11.2 Angstroms in length (U. Reineke, et al, 1999, Nature Biotechnology, 17:271) has been used to form a single peptide from two smaller discontinuous peptides of IL-10, thereby forming a TCBL which could be used for redirection from a TH1 to a TH2, in combination with, for example, the IDDM, PV or MS inducing epitopes (see Hammer, et al, supra, Tisch, et al, supra). Linkers of varying lengths to form a single chain may be used, for example, GGGS (SEQ ID NO:7), GGGGS (SEQ ID NO:9), including, from among 1 or more repeats of this tetrapeptide or pentapeptide, e.g., GGGSGGGS (SEQ ID NO:11), GGGSGTGSGSGS (SEQ ID NO:52) (See, Uger, et al. The J. of Immunology, 162: 6024–6028, 1999) etc. Such linkers may result in a tertiary structure which might be of use to form a more avid TCBL (see D. Shan, et al, supra).

Although not strictly limited, the peptide constructs of this invention may have as many as about 200 amino acids in its sequence, preferably-up to about 150 amino acids, and especially, up to about 100 amino acids. The minimum number of amino acids is also not strictly limited but usually each of the peptide components $P_1$ and $P_2$ will have at least about 4, preferably at least about 6, and more preferably at least about 8 or 9 amino acids in order to provide the appropriate epitope configuration for effectively binding to the appropriate site on the T cells of interest. Thus, the peptide constructs of this invention will usually contain from about 20 to about 100 or more amino acids.

The peptide constructs may be prepared using conventional solid state peptide synthesis, provided however, that for constructs having more than about 40 amino acids, especially more than about 50 amino acids, it is usually convenient and preferred to prepare shorter segments and then link the shorter segments using well known techniques in solid phase peptide synthesis.

Alternatively, the peptide constructs of this invention may be prepared using well known genetic engineering methods.

Further details on methods for producing the instant peptide constructs can be gleaned from the aforementioned U.S. Pat. No. 5,652,342.

The novel peptide constructs of this invention can also be used to treat transplant recipients, for example, for heart, liver, lung and kidney, who are either undergoing or at risk for rejection of the transplant (Host versus Graft or HvG). In this case, the peptide antigen(s) used to make the construct would be the major epitope(s) of the graft combined with a TCBL as described above to either suppress or redirect the immune response. As one of the major sources of antigenic materials causing the HvG are thought to be the MHC proteins and, in particular, the polymorphic regions that are from the graft tissue and recognized by the host's MHC, peptides from those regions of the graft's MHC molecules would be likely candidates for the antigenic epitope portion. Other regions of potential usefulness include polymorphic regions of the minor histocompatability antigens. TCBLs can be selected from, but are not restricted to the following LFA-3 or FasL described above (see, B. Lie, et al or Y. Tomita, et al, supra). Peptide G (SEQ ID NO:15) from the MHC II molecule, or Hu IL-10 (SEQ ID NO:28) (B. Gesser, et al, 1998, PNAS, 94:14620; Lie, et al, supra, and Y. Tomita, et al, supra) may be selected for redirection of immune responses.

As activated T cells normally express MHC molecules, another way of immunomodulation is to take advantage of the programmed pathway established by antigen addition. T cells which receive a signal from the TCR and the MHC I to CD-8⁺ cells undergo apoptosis without other costimulatory signals (S. Sambhara, et al, 1991, Science, 252:1424). Therefore, the TCBL, peptide E, (the α3 domain amino acids 223–229 of the human MHC I conserved region can be used along with the autoimmune epitope to form a peptide construct according to another embodiment of this invention.

The peptide constructs of this invention may be used as or in vaccines as therapeutic agents for treatment of autoimmune disease or HvG. The vaccines will be administered often but not always with an adjuvant and on a regular regimen such as weekly, biweekly, monthly, quarterly, semi-annually or annually by one of the following routes, ID, IM or Sub-cu and perhaps also as a cutaneous transdermal or nasal delivery vehicle in amounts of from 1–100, usually 10–50, micrograms per kilogram of body weight.

If a binding site is known on the target T cell with a defined amino acid sequence and the TCBL amino acid sequence on the ligand is not known then determination of the DNA encoding for the peptide would allow for determination of the cDNA and thus the complementary peptide sequence using the technique of Lie, et al, supra, for example.

In general, the TCBL's ($P_2$) used to form the peptide constructs of this invention will be selected from those for normal induction and modulation of immune responses, including those selected to effect redirection from Th1 or Th2, including, for example, those that are known to be related and involved in the normal events of activation, namely, IL-2, IL-10, IL-12, IL-4, IL-1β 163–171 (VQGEESNDK (SEQ ID NO:13)) (see, e.g., K. Bajpai, et al, 1998 Immunopharmacology, 38:237; W. Beckers, et al, 1993, J. Immunol., 151:1757; D. Fresca, et al, 1988, J. Immunol., 141:2651; G. Antoni, et al, 1986, J. Immunol, 187:3201), and most likely derived from the final complexes (MHC-I or II and CD8 or CD4) TCR and antigenic peptide. Examples of TCBLs that are associated with earlier activation events, include for example, Fas and FasL, TNF-α and TNF-αR and those for formation of early intermediate complexes and LFA-3 and CD2.

Examples of antigens associated with autoimmune disease, allergy, asthma, and transplantation rejection, include, for example, those mentioned above, including the Background discussion and those shown in the following, non-limiting, representative examples, as well as in the literature references cited herein, the disclosures of which are incorporated herein, in their entirety, by reference thereto. Additional examples, may also be found in the following literature, C. de Lalla, et al, 1999, J. Immunol., 163:1725 (Lol p5a allergen from rye grass); A. M. Gautam, et al, 1998, J. Immunol., 161:60 (experimental autoimmune encehpalomyelitis); as well as many others available to the practitioner.

The invention will now be described in further detail by way of representative examples, however, the present invention is not limited to the examples and should be construed to cover the subject matter as defined in appended claims and equivalents thereto.

EXAMPLE 1

A conjugated peptide NGQEEKAGVVSTGLIGGGDSAFDVLSFTAEEKAGVYK (SEQ ID NO:14) is obtained by covalently bonding Peptide G (NGQEEKAGVVSTGLI (SEQ ID NO:15)) with the cardiac myosin molecule My1 (DSAFDVLSFTAEEKAGVYK (SEQ ID NO:16)) via a GGG spacer. This peptide construct

NGQEEKAGVVSTGLIGGGDSAFDVLSFTAEEKAGVYK (SEQ ID NO:14)

can be used in a vaccine for treatment or prevention of myocarditis.

EXAMPLE 2

Addison's disease is characterized with an immune reation to the enzyme steroid 21 hydroxylase (21OH) with implication of a conformational epitope composed of peptides from the regions at 447–461 and 471–491 (see Nikoshkov et al, 1999, J. Immunol. 162:2422). Accordingly, the following peptide construct would be useful in the treatment of Addison's disease and combines the conformational epitope peptides from aa447–461 and aa474–491 of the enzyme steroid 21 hydroxylase (21OH) as a single chain linked with LRGGGGSS (SEQ ID NO:12) and the linked peptides are bounded via a GGGGS (SEQ ID NO:9) linker with a LFA-3 peptide (e.g., VLWKKQKDKVAELENSE (SEQ ID NO:4), aa 26–42 (see L. Osborn et al, J. Exp. Med. 181:429). Accordingly, the peptide construct will have the following formula:

VLWKKQKDKVAELENSE-GGGGS-21OH$_{447-461}$-LRGGGGSS-21OH$_{477-491}$
LFA-3$_{26-42}$ linker 21OH$_{447-461}$ linker 21OH$_{477-491}$ (SEQ ID NO:17)

EXAMPLE 3

The following construct will be useful in the treatment of myasthenia gravis: A TCBL from IL-10, aa.$_{152-160}$ AYMTMKIRN (SEQ ID NO:18) (see Gesser, et al, 1997, Proc. Nat. Acad. Sci. 94:14620) is linked to an epitope associated with acetylcholine receptor (AchR), EIIVTHFPFDEQNCSMK (SEQ ID NO:19), aal29–145 (see, H. Yoshikawa et al 1997 J. Immunol 159:1570) to form AYMTMKIRN-GGGGS-EIIVTHFPFDEQNCSMK
Hu-IL-10$_{152-160}$ linker AchR$_{129-145}$ (SEQ ID NO: 20)

Similar results can be obtained by using as the TCBL, in place of Hu-IL$_{152-160}$, the MHC I α3 domain peptide 223–229 (DQTQDTE (SEQ ID NO:21)) that binds to the CD8 molecule, to form the following construct:

DQTQDTE-GGGGS-EIIVTHFPFDEQNCSMK
MHC-1α$_{223-229}$ linker AchR$_{129-145}$ (SEQ ID NO: 22)

EXAMPLE 4

Rheumatoid arthritis (RA), is a condition where excess Tumor necrosis factor-α (TNF-α) production is a problem and a major point of attack for new treatments. The following peptide construct is prepared for use in the treatment of RA:

PSTHVLITHTI-GGG-IAGFKGEQGPKGE
TNF-α$_{70-80}$ linker C-II$_{390-402}$ (SEQ ID NO: 23)

where the peptide TNF-α$_{70-80}$ is known to activate macrophages (10) and the collagen type II peptide C-II$_{390-402}$ (IAGFKGEQGPKGE (SEQ ID NO:40)) is an epitope associated with RA. Thus, this peptide construct will be useful to achieve abortative T cell modulation since the improper sequence of events occurs with a binding that precludes the normal activation process.

Similar effects will be achieved using a peptide construct similar to the above but obtained by using, in place of TNF-α peptide α$_{70-80}$, the following: TNF-α antagonist: DFLPHYSLGHRP (SEQ ID NO:24) (see C. Chirinos-Rojas et al, J. Immunol 161:5621), namely, DFLPHYKNTSLGHRP-GGG-IAGFKGEQGPKGE
TNF-α$_{antagonist\ peptide}$ spacer C-II$_{390-402}$ (SEQ ID NO:25)

EXAMPLE 5

As a different approach for treating RA the following peptide construct is prepared utilizing peptide G or a derivative thereof (derG) (DGQEEKAGVVSTGLI (SEQ ID NO:50)) from MHC-IIβ2(135–149) to redirect the immune response from a TH1 to a TH2:

NGQEEKAGVVSTGLI-GGGGS-IAGFKGEQGPKGE
G(MHC-IIβ2) linker C-II$_{390-402}$ (SEQ ID NO:26)

or

DGQEEKAGVVSTGLI-GGGGS-IAGFKGEQGPKG
derG(MHC-IIβ2) linker C-II$_{390-402}$ (SEQ ID NO:27)

EXAMPLE 6

Another example of a peptide construct according to this invention for redirecting the immune response from a TH1 to a TH2, is used in the treatment of autoimmune myocarditis is obtained by linking as a TCBL the single chain construct (see D. Shan et al, 1999, J. Immunol., 162:6589) using the discontinuous regions of Hu IL-10 having the sequence DNQLLETCKQDRLRNRRGNGSSTHFEGN-LPC (SEQ ID NO:28) with the cysteines at aa8 and 31 cyclized in a disulfide bond ring (see, e.g., U. Reinke et al, 1999, Nature Biotechnology, 17:271) linked via a GGGGS (SEQ ID NO:9) spacer to an autoimmune epitope from My-1 from murine cardiac myosin (see D. L. Donermeyer, et al, 1995, J. Exp. Med., 182:1291) or the human counterpart:

DNQLLETCKQDRLRNRRGNGSSTHFEGNLPC-
GGGGS-DSAFDVLSFTAEEKAGVYK

Hu IL-10 discontinuous epitopes linker My-I$_{334-352}$ (SEQ ID NO:29)

EXAMPLE 7

This example shows a peptide construct for treating autoimmune response associated with the myelinproteolipid protein (MPLP) having the sequence VHFFKNIVTPRTP (SEQ ID NO:41) using the MHC-Iα$_{223-229}$ TCBL:

DQTQDTE-GGGGSS-VHFFKNIVTPRTP
MHC linker MPLP
–Iα$_{223-229}$ (SEQ ID NO:30)

EXAMPLE 8

This example illustrates an embodiment of a peptide construct useful in treating an autoimmune disease, thrombosis, by allowing initiation of an immune response but not allowing full development and completion.

In particular, the peptide GDKVSFFCKNKEKKC (SEQ ID NO:3) for antiphospholipid (PL) antibodies associated with thrombosis (see Gharavi, et al, 1999, J. Immunol. 163:2922) is linked to a MHC-I TCBL as previously described:

DQTQDTE-GGGGSS-GDKVSFFCKNKEKKC
MHC-Iα$_{223-229}$ linker PL (SEQ ID NO:31)

EXAMPLE 9

This example illustrates a peptide construct for redirecting the immune response from IgE to another more benign immune response. Similar peptide constructs to that shown below would be useful to treat various allergic conditions resulting from allergy epitopes, including, for example, pollens, such as from grasses and trees; venoms, such as from bee venom; danders such as from cow, cat, dog, rabbit, mouse, rat, and other household pets; and dust mite antigens, simply by replacing the exemplified Bos d2 allergen peptide with the appropriate allergen peptide.

DQTQDTE-GGGGSS-YQQLNSERGVPNENIEN
MHC-Iα$_{223-229}$ linker Bos d2$_{131-148}$ (SEQ ID NO:32)

where Bos d2$_{131-148}$ (YQQLNSERGVPNENIEN (SEQ ID NO:42)) is the cow dander allergen of Lipocalin, epitope "G" at carboxyl terminus (T. Zeiler et al 1999, J. Immunol. 162:1415).

EXAMPLE 10

Another approach to a peptide conjugate for treating allergic conditions is achieved with the following peptide conjugate which will initiate recognition and the activation process but without allowing reorientation and, therefore, will cause truncation of the immune response with premature cessation, resulting in cell anergy and apoptosis.

VLWKKQKDKVAELENSE-
GGGGSS-IQTQMKTYSDIDGKLVSEV
LFA-3$_{26-42}$ linker ParJ1$_{47-65}$ (SEQ ID NO.33)

where ParJ1$_{47-65}$ (IQTQMKTYSDIDGKLVSEV (SEQ ID NO:43)) is a pollen antigen from the common plant from the mediterian region of *Parietaria judaaica* (R. De Palme et al J. Immunol. 162:1836).

EXAMPLE 11

Similarly to the peptide construct of Example 10, the following peptide constructs would similarly cause T cell activation followed by premature cessation of the immune response:

VLWKKQKDKVAELENSE-
GGGGSS-VFIKRVSNVIIHG
LFA-3$_{26-42}$ linker Cry j1$_{108-120}$ (SEQ ID NO:34) where Cry j1$_{47-65}$ (VFIKRVSNVIIHG (SEQ ID NO:44)) is the Japanese cedar pollen antigen from *Cryptomeria Japonica*, aa47–65;

VLWKKQKDKVAELENSE-
GGGGSS-MKVTVAFNQFGPNRR
LFA-3$_{26-42}$ linker Cry j1$_{121-225}$ (SEQ ID NO: 35)

where Cry j1$_{211-225}$ (MKVTVAFNQFGPNRR (SEQ ID NO:45)) is the Japanese cedar pollen antigen from *Cryptomeria Japonica*, aa221–225;

VLWKKQKDKVAELENSE-
GGGGSS-IASRRVDGIIAAYQN
LFA-3$_{26-42}$ linker Cry j2$_{66-80}$ (SEQ ID NO:36)

where Cry j2$_{66-90}$ (IASRRVDGIIAAYQN (SEQ ID NO:46)) is the Japanese cedar pollen antigen from *Cryptomeria Japonica*, Cry j2, aa66–80;

VLWKKQKDKVAELENSE-
GGGGSS-IDIFASKNFHLQKNTIGTG
LFA-3$_{26-42}$ linker Cry j2$_{182-200}$ (SEQ ID NO:37)

where Cry j3$_{26-42}$ (IDIFASKNFHLQKNTIGTG (SEQ ID NO:47)) is the Japanese cedar pollen antigen from *Cryptomeria* Japonica, Cry j2, aa182–200 (see, e.g., T. Sone, et al, 1998, J. Immunol., 161:448).

Similarly, by replacing the allergen antigen in the above conjugated peptides with, for example, the allergen antigen from other plants, grasses and trees, other conjugated peptides effective in the treatment of the associated allergic condition will be obtained. Examples of such other allergen antigens include olive tree *Olea europea* pollen (located in a 17 kDa protein, P. Lauzurica et al, 1988, Mol. Immunol. 25:329); rye grass pollen *Lolium perenne*, major epitope shared between Lol p I, II, III (Ansari, et al, 1987, J. Immunol. 139:4034) and Lol p 5a$_{145-170}$ (Schramm et al, 1999, J. Immunol. 162:2406); Timothy grass pollen rPh1 p1, p2, p5$_{85-120}$ and p5$_{210-240}$.

EXAMPLE 12

Other peptide constructs useful in the treatment of allergic conditions associated with dust mite antigens, are prepared by linking TCBLs, such as LFA-3 or MHC-1α, with, for example, fecal allergen of mite *Dermatophagoides* pteronyssimus Der p1 and related mites, known to induce an IgE reaction (Lind et al 1988 J. Immunol. 140:4256; Platts-Mills et al 1987 J. Allerg. Clin. Immunol 80:755), but redirected in accordance with this invention. Moreover, since it is known that Der p1 and Der p9 trigtger release of GmCSF, IL-6, IL-8, etc. (C. King et al 1998 J. Immunol. 161:3645), these constructs with LFA-3 or MHC-1α would be expected to be of benefit by the activation/truncation mechanism leading to cell anergy and apoptosis as previously described.

EXAMPLE 13

VLWKKQKDKVAELENSE-
    GGGGSS-YFVGKMYFNLID

LFA-3$_{26-42}$ linker PLA A2$_{81-92}$ (SEQ ID NO:38)

where PLA A2$_{81-92}$ (YFVGKMYFNLID (SEQ ID NO:48)) is a bee venom antigen (A. Faith et al 1999 J. Immunol 162:1836) or

DQTQDTE-
    GGGGSS-GIGAVLKVLTTGPALISWIKRKRQQ

MHC-Iα linker Melittin (SEQ ID NO:39)

where Melittin (GIGAVLKVLTTGPALISWIKRKRQQ (SEQ ID NO:49)) is a Honey Bee antigen which has been shown to induce IgE in about ⅓ of bee allergic persons (T. P. King et al 1994, J. Immunol. 153:1124); are peptide constructs according to the invention which can be administered to bee allergic persons to protect such treated individuals against allergic reactions resulting from bee stings.

What is claimed is:

1. An immunomodulatory peptide construct with the formula $P_1$-X-$P_2$ where $P_1$ is a peptide associated with autoimmune disease, allergy or asthma, or host-versus-graft rejection and which will bind to an antigen receptor on a set or subset of T cells;

$P_2$ is an immune modulating peptide which will (i) cause a directed immune response by said set or subset of T cells to which the peptide $P_1$ is attached or (ii) bind to a T cell receptor which will cause said set or subset of T cells to which the peptide $P_1$ is attached to initiate, but not complete, an immune response causing said set or subset of T cells to undergo anergy and apoptosis; and x is a direct bond or linker for covalently bonding $P_1$ and $P_2$ wherein the immunomodulatory peptide construct with the formula $P_1$-X-$P_2$ is selected from the group consisting of SEQ ID NO: 14, SEQ ID NO: 17, SEQ ID NO: 20, SEQ ID NO: 22, SEQ ID NO: 23, SEQ ID NO: 25, SEQ ID NO: 26, SEQ ID NO: 27, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38 and SEQ ID NO: 39.

* * * * *